United States Patent [19]

Kobayashi et al.

[11] Patent Number: 4,871,840

[45] Date of Patent: Oct. 3, 1989

[54] HETEROGENEOUS MULTIPLE-BRANCHED CYCLODEXTRIN AND METHOD FOR THE PREPARATION THEREOF

[75] Inventors: Shoichi Kobayashi, Tsuchiura; Masaomi Arahira, Tsukuba, both of Japan

[73] Assignee: Director of National Food Research Institute Ministry of Agriculture, Forestry and Fisheries, Tsukuba, Japan

[21] Appl. No.: 151,805

[22] Filed: Feb. 3, 1988

[30] Foreign Application Priority Data

Sep. 17, 1987 [JP] Japan ................................ 62-231073

[51] Int. Cl.[4] ...................... C12P 19/18; C12P 19/22; C12P 19/16
[52] U.S. Cl. .................................................. 536/103
[58] Field of Search .................... 536/103; 435/74, 94, 435/25, 96, 97, 98, 99

[56] References Cited

U.S. PATENT DOCUMENTS 4,604,355 8/1986 Outtrup ................................ 435/95
4,668,626 5/1987 Kobayashi et al. .................. 436/97

*Primary Examiner*—John Kight
*Assistant Examiner*—Nathan M. Nutter
*Attorney, Agent, or Firm*—Frishauf, Holtz, Goodman & Woodward

[57] ABSTRACT

Different from conventional heterogeneous multiple-branched cyclodextrins having branches derived from the same kind of saccharide molecule, the inventive heterogeneous multiple-branched cyclodextrin has branches derived from different kinds of saccharides of, one, glucose and, the other, a maltooligosaccharide. The inventive heterogeneous multiple-branched cyclodextrins are more stable than conventional ones and useful as an ingredient of medical, foodstuff and cosmetic preparations. The heterogeneous multiple-branched cyclodextrin can be prepared from a mixture of a maltooligosaccharide and a glucosyl cyclodextrin by the reverse action of debranching enzyme.

8 Claims, 2 Drawing Sheets (a)

(b)

Elution Time (minute)

4,871,840

HETEROGENEOUS MULTIPLE-BRANCHED CYCLODEXTRIN AND METHOD FOR THE PREPARATION THEREOF

BACKGROUND OF THE INVENTION

The present invention relates to a branched cyclodextrin or, more particularly, to a heterogeneous multiple-branched cyclodextrin (HEMB-CD) of which the branched portion of the molecular structure is composed of a combination of different saccharide moieties as well as to a method for the preparation of such HEMB-CD.

As is known, branched cyclodextrins have various excellent properties such as high solubility so that intensive investigations are under way on the method for the preparation and application development thereof. As a result of the hitherto undertaken investigations, several kinds of branched cyclodextrins have been reported including single-branched cyclodextrins in which the cyclodextrin ring has only one branched dextrin molecule bonded thereto such as α-1,4-glucans, e.g., glucose and maltose, panose and the like and HEMB-CD in which the cyclodextrin ring has two or more branches of the same saccharide molecules bonded thereto such as glucose, maltose and maltooligosaccharides, e.g., maltotriose. Exemplary of known heterogenous multiple-branched cyclodextrins are diglucosyl cyclodextrin of which a cyclodextrin ring has two glucosyl branches and dimaltosyl cyclodextrin of which a cyclodextrin ring has two maltosyl branches bonded thereto.

These heterogeneous multiple-branched cyclodextrins are prepared enzymatically from a branched cyclodextrin with an enzyme for cyclodextrin synthesis or from a mixture of a branched dextrin such as an α-1,4-glucan, e.g., maltose and maltotriose, panose and the like and a cyclodextrin and the reverse action of debranching enzyme.

Although single-branched cyclodextrins in general have a greatly increased solubility as compared to the starting cyclodextrin, some of the rings have only an insufficient effect on the increase of the solubility. Therefore, it is an important technical problem to develop various branched cyclodextrins having a branched structure of different saccharides bonded in different manners and to study the properties thereof.

Further, single-branched cyclodextrins such as single-branched β-cyclodextrins are susceptible to the enzymatic activity of the starch-degrading enzyme, i.e. Takaamylase of *Aspergillus oryzae* so that it is increasingly demanded to develop a cyclodextrin compound highly resistant against the enzymatic activity of these enzymes.

As to the HEMB-CD, no heterogeneous multiple-branched cyclodextrin is known in the prior art of which a single cyclodextrin ring has two or more branches bonded thereto as derived from differnt kinds of saccharides such as glucose, maltose and the like. Much less, absolutely no information is available on the method for the preparation of such HEMB-CD.

It is a known art that the reverse reaction of a debranching enzyme such as pullulanase and the like can be utilized for the preparation of maltosyl cyclodextrins, maltotriosyl cyclodextrins, panosyl cyclodextrins, dimaltosyl cyclodextrins and the like from a combination of a cyclodextrin and maltose, maltotriose, panose and the like. Although this knowledge has been utilized to establish the method for the preparation of single-branched and heterogeneous multiple-branched cyclodextrins, it is not known that heterogeneous multiple-branched cyclodextrins are formed from a maltooligosaccharide and a glycosyl cyclodextrin by the reverse reaction of a debranching enzyme.

SUMMARY OF THE INVENTION

The present invention accordingly has an object to provide a novel HEMB-CD by utilizing the above mentioned enzymatic reaction.

Thus, the novel cyclodextrin compound provided by the present invention is a HEMB-CD which is a branched cyclodextrin having a branched structure formed of a combination of the moieties of glucose and a maltooligosaccharide bonded to the cyclodextrin ring.

In particular, the above mentioned maltooligosaccharide is selected from maltose, maltotriose, maltotetraose, maltopentaose, maltohexaose, panose and glucosyl maltotriose and the cyclodextrin ring has a structure of α-, β- or δ-cyclodextrin.

The above defined HEMB-CD of the invention can be prepared by subjecting a mixture composed of a maltooligosaccharide or a saccharide mixture containing the same and a glucosyl cyclodextrin to the reverse action of a debranching enzyme.

BRIEF DESCRIPTION OF THE DRAWING

FIGS. 1a, 1b and 1c are each a schematic illustration of the molecular structure of HEMB-CD, of which FIG. 1a is of a glucosyl maltosyl cyclodextrin, FIG. 1b is of a glucosyl maltotriosyl cyclodextrin and FIG. 1c is of a glucosyl panosyl cyclodextrin. In the figures, the small circle shows a glucose residue, the large double circle shows a cyclodextrin ring, the horizontal line shows an α-1,4-linkage and the vertical arrowed line shows an α-1,6-linkage.

DETAILED DESCRIPTION OF THE PREFERRED EMBODIMENTS

Figure 1:
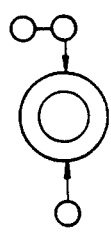
Figure 1:
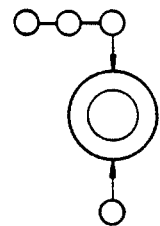
Figure 1:
Figure 2:
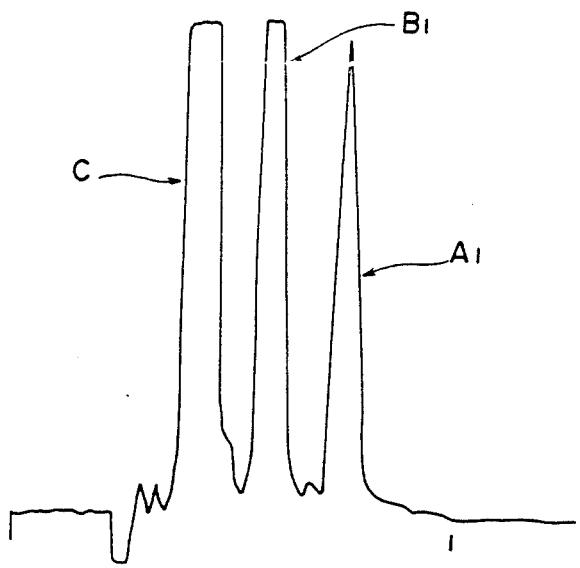
FIGS. 2a and 2b are each an elution diagram obtained in the high-performance liquid chromatography of the glucosyl maltosyl β-cyclodextrin and glycosyl maltosyl α-cyclodextrin, respectivelly, prepared from maltose and glucosy β- or α-cyclodextrin. In the figure, $A_1$ shows glucosyl maltosyl-β-cyclodextrin; $A_2$ shows glucosyl maltosyl-α-cyclodextrin; $B_1$ shows unreacted glucosyl-β-cyclodextrin; $B_2$ shows unreacted glucosyl-α-cyclodextrin; and C shows maltose, respectively.
Figure 2:
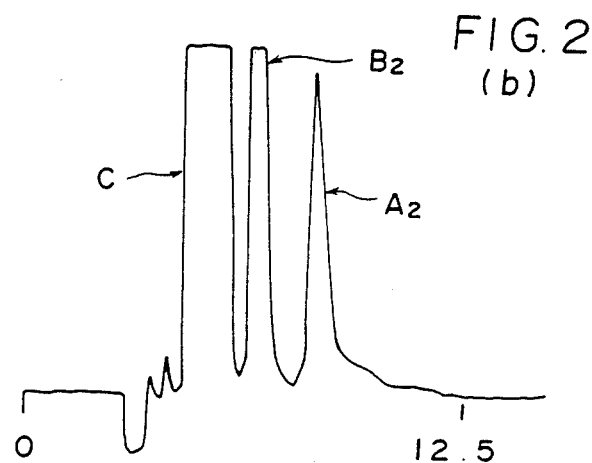

The present invention summarized above has been completed on the basis of an unexpected discovery of the inventors that a heterogeneous multiple-branched cyclodextrin, of which one and the same cyclodextrin ring has two or more branches derived from glucose and a maltooligosaccharide bonded thereto, can be otained by the reverse action of debranching enzyme on a mixture composed of a glucosyl cyclodextrin and a maltooligosaccharide such as maltose, maltotriose, maltotetraose, maltopenaose, maltohexaose, panose, glucosyl maltotriose and the like.

The maltooligosaccharide implied in this invention includes the linear-chain α-1,4-glucans such as maltose, maltotriose and the like and branched maltooligosaccharides having an α-1,6-branch such as panose and the like.

As is mentioned above, the present invention relates, on one hand, to HEMB-CD of which the branch portion of a branched cyclodextrin is a heterogeneous multiplicity of branches derived from glucose and a maltooligosaccharide and, on the other hand, to a method for the preparation of such HEMB-CD comprising the reverse action of debranching enzyme on a mixture of a maltooligosaccharide or a saccharide mixture containing the same and a glucosyl cyclodextrin.

The HEMB-CD here implied is a special branched cyclodextrin having two kinds or more of different branches. In particular, a glucosyl cyclodextrin derivative having a molecule of a maltooligosaccharide bonded thereto can be obtained by the reverse action of debranching enzyme on a mixture of a glucosyl cyclodextrin and one or more of maltooligosaccharides selected from the group consisting of maltose, maltotriose, maltotetraose, maltopentaose, maltohexaose, panose, glucosyl maltotriose and the like.

The branched portion of the inventive HEMB-CD is formed of a combination of two kinds or more of glucose and maltooligosaccharides including maltose, maltotriose, maltotetraose, maltopentoase, maltohexaose, panose, glucosyl maltotriose and the like. In the inventive HEMB-CD, in particular, the branches are typically derived, one, from glucose and, the other, from a mulltooligosaccharide. Such HEMB-CD having branches derived from two kinds or more of different saccharides is sometimes called a heterogeneous multiple-branched cyclodextrin while conventional multiple-branched cyclodextrins, of which the branches are derived from a single kind of a saccharide compound, are called homogeneous multiple-branched cyclodextrin (HOMB-CD).

Several kinds of debranching enzymes can be used for the preparation of the inventive HEMB-CD including pullulanase, isoamylase and the like produced by various kinds of microorganisms.

The conditions of the reverse action should be selected so as to give the highest yield of the desired HEMB-CD. Assuming that the final concentrations of maltose and glucosyl β-cyclodextrin are 50% and 10%, respectively, for example, a reaction carried out for 2 to 7 days with addition of a commercial product of pullulanase in an amount of 30 to 100 IU gives the desired HEMB-CD in a yield of 10 to 30%.

In an example, the chemical structure of the thus obtained HEMB-CD was studied by subjecting the material in a low concentration of 5% or below to an enzymatic reaction with a debranching enzyme and analyzing the reaction products by the high-performance liquid chromatography and paper chromatography. The results of the analysis indicated that the molar ratio of the glucosyl cyclodextrin and maltooligosaccharide was 1:1 and the HEMB-CD had a structure in which a cyclodextrin ring had each a molecule of glucose and maltooliogosaccharide moieties bonded through α-1,6-linkages.

Besides, certain debranching enzymes of different kinds may possibly produce HEMB-CD having branches derived from three saccharide molecules.

The maltooligosaccharide subjected to branch formation by the debranching enzyme should have a maltosyl or larger α-1,4-glucan chain at the reduced terminal thereof while a branch and a modifying group should be bonded to the glucose residue other than that at the reduced terminal.

Furthermore, branch formation may take place, in place of the glucosyl cyclodextrin, in certain derivatives of cyclodextrin such as methylated cyclodextrin, hydroxyethyl cyclodextrin and the like to give, for example, maltosyl methylcyclodextrin.

It would be possible to produce various kinds of HEMB-CD by the reverse acttion of a debranching enzyme on a mixture of two maltooligosaccharides taken in a combination as desired in a proportion also as desired. For example, the enzymatic reaction of a mixture of maltose and maltotriose may lead to the formation of HEMB-CD having branches derived from maltose and maltotriose.

Besides, the invention may provide a method for the preparation of different HEMB-CD in which the reverse action of a debranching enzyme is performed with a mixture of two kinds or more of glucose and maltooligosaccharides having fluorine atoms bonded to the carbon atoms, i.e. glucosyl fluoride, or a mixture of a glucosyl fluoride and an ordinary maltooligosaccharide.

The glucosyl cyclodextrin can be obtained by fractionating a reaction mixture after the enzymatic reaction of a mixture of a cyclodextrin and maltose in the presence of pullulanase by the reversed-phase column chromatography on a column of ODS and the like into the fractions of maltose, unreacted cyclodextrin, maltosyl cyclodextrin and dimaltosyl cyclodextrin followed by the enzymatic reaction of maltosyl cyclodextrin in the presence of glucoamylase. The glucose produced here can be removed by the column chromatography on an ODS column or by a treatment with yeast but the reaction mixture containing glucose can be used as such in many applications.

The debranching enzymes usable in the inventive method include pullulanase, isoamylase and the like of various microbial origins and selection amoung them depends on the chain length of the maltooligosaccharide moiety which should be the branch on the cyclodextrin ring. As a general rule, pullulanase is preferred when the maltooligosaccharide to be the branch has a short chain length while both of pullulanase and isoamylase can be used for the branch-forming reaction of a maltooligosaccharide having a long chain length.

The heterogeneous multiple-branched cyclodextrins can be obtained in the above described manner from various kinds of starting materials but the content thereof in the reaction mixture depends also on the kind of the starting material. Namely, the amount of production of HEMB-CD depends on the contents of the glycosyl cyclodextrin and the maltooligosaccharide to be the branch on the cyclodextrin ring. In order to obtain HEMB-CD in a high yield, accordingly, it is more advantageous to use a saccharide syrup containing the desired saccharide in a higher concentration. Desirably, the saccharide syrup should be used after increasing the content of the desired saccharide by a suitable mthod such as enrichment by precipitation with an organic solvent such as acetone, ethyl alcohol and the like, removal of glucose and disaccharides by assimilation with yeast, separation by column chromatography and so on.

In the following, the present invention is described in more detail by way of examples.

EXAMPLE 1

A reaction mixture in a volume of 1 ml having a pH of 5.0 was prepared by adding 100 mg of a glucosyl β-cyclodextrin prepared by the inventors and 500 mg of maltose into 100 μl of a 0.1M acetate buffer solution and 200 μl of a pullulanase solution of 100 U/ml followed by dilution with water. The pullulanase solution was obtained by subjecting a commercial product of pullulanase supplied by Novo Co. to dialysis overnight in a 50 mM acetate buffer solution. The enzymatic reaction was performed for 3 days at 55° C. to give a glucosyl maltosyl β-cyclodextrin in a yield of 23%.

The analysis of the reaction mixture was undertaken by the high-performance liquid chromatography on a 5 μm Rechrocart-NH2 column using 1 μl of the reaction mixture with a 50% acetonitrile as the eluant solution at a flow rate of 0.8 ml/minute. The above mentioned yield was calculated relative to the amount of the glucosyl cyclodextrin used as the starting material.

EXAMPLE 2

The experimental procedure was substantially the same as in Example 1 except that the glucosyl β-cyclodextrin was replaced with glucosyl α-cyclodextrin to give glucosyl maltosyl α-cyclodextrin in a yield of 12%.

EXAMPLE 3

The experimental procedure was substantially the same as in Example 1 except that the glucosyl β-cyclodextrin was replaced with glucosyl γ-cyclodextrin to give glucosyl maltosyl γ-cyclodextrin in a yield of 32%.

EXAMPLE 4

The experimental procedure was substantially the same as in Example 1 except that the maltose was replaced with panose to give glucosyl panosyl β-cyclodextrin in a yield of 15%.

As is described in detail, the resent invention provides a method for efficiently producing various kinds of novel HEMB-CD. Among these HEMB-cyclodextrins, the HEMB-β-, HEMB-γ-cyclodextrins are useful as a base of medicament forms because the cyclodextrin ring thereof, which is otherwise susceptible to the enzyme action of starch degrading enzymes such as Takaamylase and the like, is stabilized to be insusceptible or hardly susceptible to the enzyme action of α-amylase. Furthermore, they are very promising as a new material useful in a wide fields of applications for foods, cosmetic preparations and the like because of the possible increase in the clathrate effect by the synergistic effect of the hollow of the cyclodextrin ring and the branches bonded thereto.

As compared to conventional cyclodextrins, in particular, the HEMB-cyclodextrins have further decreased digestibility so that they are promising in applications of health-promoting foods and special foods for corpulence prevention or as a proliferation factor of bifidus bacteria.

Different preparation processes produce products of the HEMB-CD in varied concentrations together with the glucosyl cyclodextrin and maltooligosaccharide used as the starting materials, glucose, cyclodextrin and the like.

When HEMB-CD of high purity is desired, the reaction mixture is subjected to a conventional purification process such as the reversed-phase column chromatography on ODS and the like, precipitation by the addition of a solvent and the like.

When Takaamylase is used as the enzyme either alone or as combined with glucoamylase, diglucosyl β- and γ-cyclodextrins can be produced efficiently in the reaction mixture of HEMB-CD β- and γ-cyclodextrins and can be isolated therefrom.

What is claimed is:

1. A heterogeneous multiple-branched cyclodextrin which is a branched cyclodextrin having a branched structure formed of a combination of the moieties of glucose and a maltooligosaccharide bonded to the cyclodextrin ring.

2. The heterogeneous multiple-branched cyclodextrin as claimed in claim 1 wherein the maltooligosaccharide is selected from the group consisting of maltose, maltotriose, maltotetraose, maltopentaose, maltohexaose, panose and glucosyl maltotriose.

3. The heterogeneous multiple-branched cyclodextrin as claimed in claim 1 wherein the cyclodextrin ring has a structure of α-, β- or γ-cyclodextrin.

4. The heterogeneous multiple-branched cyclodextrin as claimed in claim 3 wherein the maltooligosaccharide is selected from the group consisting of maltose, maltotriose, maltotetraose, maltopentoase, maltohexaose, panose and glucosyl maltotriose.

5. A method for the preparation of a heterogeneous multiple-branched cyclodextrin which comprises subjecting a mixture of a maltooligosaccharide or a saccharide mixture containing the same and a glucosyl cyclodextrin to a reverse action of debranching enzymes.

6. The method for the preparation of a heterogeneous multiple-branched cyclodextrin as claimed in claim 5 wherein the heterogeneous multiple-branched cyclodextrin is a branched cyclodextrin having a branched structure formed of a combination of the moieties of glucose and a maltooligosaccharide bonded to the cyclodextrin ring.

7. The method for the preparation of a heterogeneous multiple-branched cyclodextrin as claimed in claim 5 wherein the cyclodextrin ring has a structure of α-, β- or γ-cyclodextrin.

8. The method for the preparation of a heterogeneous multiple-branched cyclodextrin as claimed in claim 6 wherein the heterogeneous multiple-branched cyclodextrin is branched cyclodextrin having a branched structure formed of a combination of the moieties of glucose and a maltooligosaccharide bonded to the cyclodextrin ring.

* * * * *